(12) United States Patent
Young et al.

(10) Patent No.: US 10,639,069 B2
(45) Date of Patent: May 5, 2020

(54) RADIAL SUPPORT ASSEMBLY FOR A TROCAR ASSEMBLY

(71) Applicant: Ethicon LLC, Guaynabo, PR (US)

(72) Inventors: Joshua Young, Loveland, OH (US); Stephanie Toy, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 174 days.

(21) Appl. No.: 15/720,574

(22) Filed: Sep. 29, 2017

(65) Prior Publication Data

US 2019/0099200 A1    Apr. 4, 2019

(51) Int. Cl.
*A61B 17/34* (2006.01)
(52) U.S. Cl.
CPC ...... *A61B 17/3462* (2013.01); *A61B 17/3417* (2013.01); *A61B 17/3474* (2013.01); *A61B 2017/347* (2013.01)
(58) Field of Classification Search
CPC ............ A61B 17/3462; A61B 17/3417; A61B 2017/347; A61B 17/3474; A61B 17/34; A61B 17/3421; A61B 17/3439
See application file for complete search history.

(56) References Cited

U.S. PATENT DOCUMENTS

| | | | |
|---|---|---|---|
| 8,870,904 B2 * | 10/2014 | Taylor | A61B 17/3423 606/185 |
| 2008/0287877 A1 | 11/2008 | Gresham | |
| 2009/0076456 A1 | 3/2009 | Armstrong et al. | |
| 2012/0116313 A1 | 5/2012 | Franer et al. | |
| 2015/0250498 A1 * | 9/2015 | Kikuchi | A61B 17/3417 604/67 |

FOREIGN PATENT DOCUMENTS

| | | | |
|---|---|---|---|
| WO | 94/17844 A1 | 8/1994 | |
| WO | 01/89397 A1 | 11/2001 | |
| WO | WO-0189397 A1 * | 11/2001 | A61B 17/3462 |
| WO | 2011/082114 A1 | 7/2011 | |
| WO | 2016/144180 A1 | 9/2016 | |
| WO | WO-2016144180 A1 * | 9/2016 | A61B 17/34 |

OTHER PUBLICATIONS

ISRWO of corresponding PCT/IB2018/057317 dated Oct. 12, 2018.

* cited by examiner

*Primary Examiner* — Amber R Stiles
(74) *Attorney, Agent, or Firm* — Vorys, Sater, Seymour and Pease LLP

(57) ABSTRACT

A trocar assembly includes a trocar housing that defines a working chamber, and a cannula having a proximal end and a distal end, wherein the cannula is coupled to the trocar housing at the proximal end to facilitate communication between the cannula and the working chamber. A radial support assembly is arranged at or near the distal end and includes a plurality of radial support members that extend radially inward toward a centerline of the cannula to center a surgical tool within the cannula and thereby minimize unintended oscillation and vibration of the surgical tool.

9 Claims, 11 Drawing Sheets

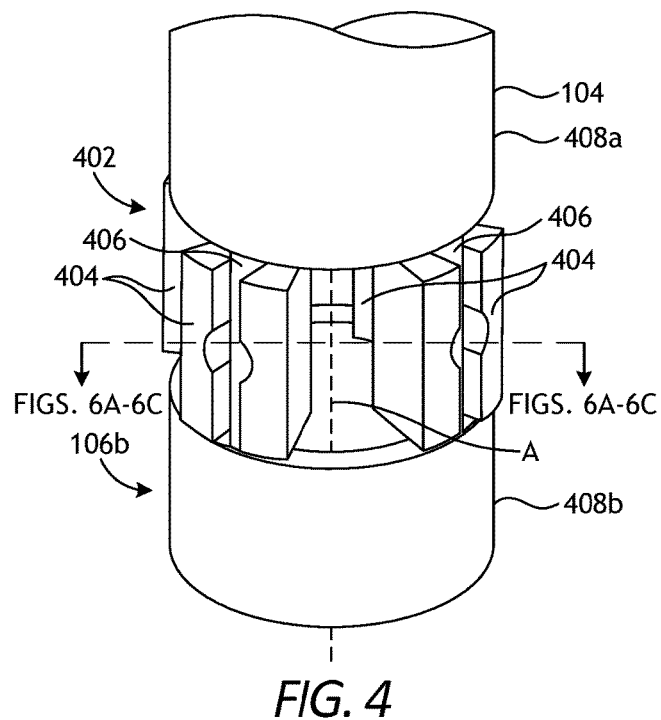
FIG. 4
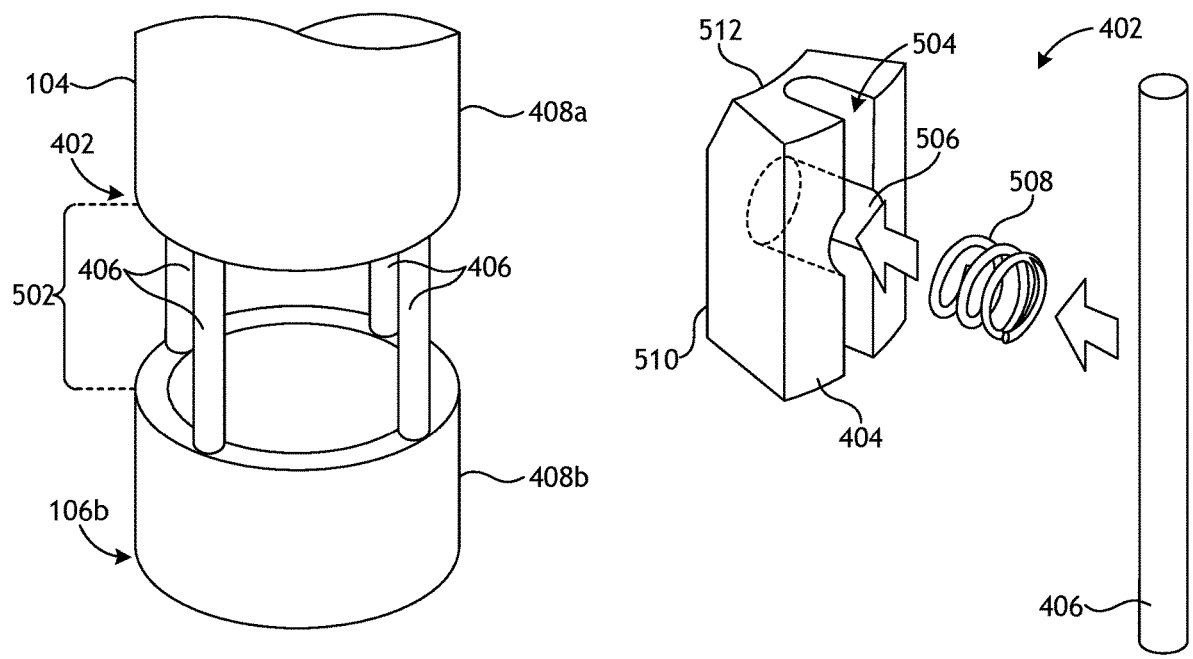
FIG. 5A
FIG. 5B

US 10,639,069 B2

RADIAL SUPPORT ASSEMBLY FOR A TROCAR ASSEMBLY

BACKGROUND

During laparoscopic surgery, one or more small incisions are formed in the skin of a patient and a trocar assembly is inserted through the incision to form a pathway that provides access to an internal body cavity, such as the patient's abdomen. The trocar assembly is used to introduce various instruments and tools into the abdomen, as well as to provide insufflation that elevates interior walls of the abdomen.

A trocar assembly generally includes a housing, a cannula that extends from the housing, and an obturator that can be inserted into the housing and the cannula. To set the trocar assembly for a surgical operation, the obturator is extended through an interior lumen of the cannula and is used to pierce through the patient's skin to access the abdominal cavity. To penetrate the skin, the distal end of the cannula is placed against an incision in the skin and pressure is applied to the proximal end of the trocar to force the sharp point of the obturator through the skin until it enters the targeted body cavity. The obturator can then be withdrawn, leaving the interior lumen of the cannula as a path to access the abdominal cavity from outside the body.

The trocar housing is attached to the proximal end of the cannula and defines a working chamber with an open distal end in communication with the interior lumen of the cannula. Just as the interior lumen can receive the obturator, it is also sized to receive elongated surgical tools that are axially extended into and withdrawn from the cannula through the proximal end portion of the working chamber.

For surgical operations, a surgeon will normally use a 1:1 pairing of a trocar assembly and a surgical tool. For example, if an 8 mm (diameter) surgical tool is required for an operation, a corresponding 8 mm (diameter) trocar assembly will be used. In robotic surgery, however, trocar assemblies and surgical tools will not always enjoy a 1:1 pairing. For example, 12 mm (diameter) trocar assemblies are typically used in robotic surgery, which enables use of 12 mm (diameter) surgical tools, such as a surgical stapler. Yet some procedures require an 8 mm or 5 mm (diameter) surgical tool, which will have to pass through the 12 mm trocar assembly.

When the trocar assembly and surgical tool pairing is not 1:1, there can be "lost motion" or hysteresis to the movement where the tip (distal end) of the surgical tool is prone to various types of unintended motion, such as deflection, oscillation in place, and spring back oscillation. For instance, the initial movement input to the robot by the surgeon will not move the surgical tool, but will instead first remove the clearance between the instrument and the trocar assembly, and will subsequently move the surgical instrument. This lost motion is unacceptable to the surgeon, who expects fine control and precision from the surgical robot. The clearance between the trocar assembly and the smaller diameter surgical instrument can also result in the surgical instrument vibrating without hitting the inner walls of the trocar assembly.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 4 depicts an example radial support assembly that may be incorporated into the trocar assembly of FIGS. 1-3.

FIG. 5A shows the radial support assembly of FIG. 4 without the radial support members.

FIG. 5B is an exploded view of a portion of the radial support assembly of FIG. 4.

DETAILED DESCRIPTION

The present disclosure is related to trocar assemblies and, more particularly, to radial support assemblies that include a plurality of radial support members used to center surgical tools within a trocar cannula of a trocar assembly and mitigate unwanted oscillation and vibration.

The embodiments described herein provide a radial support assembly that can be incorporated into a trocar assembly at or near the distal end of a trocar cannula. The radial support assembly helps eliminate or significantly minimize unintended oscillation movement and vibration of smaller surgical tools. Moreover, the radial support assembly may also be compliant so that it is able to accommodate larger diameter surgical tools. The radial support assembly includes a plurality of radial support members that extend radially inward toward a centerline of the cannula to center a surgical tool within the cannula. In some embodiments, the radial support members may be radially compliant and therefore, able to accommodate varying diameters of surgical tools that may be used in the trocar assembly. In other embodiments, the radial support members may be keystone-shaped and arranged side by side to form a ring within the trocar cannula. Some of the radial support members extend inward to a first depth, while others extend inward to a second depth. This allows the radial support assembly to accommodate varying diameter surgical tools. When larger-diameter surgical tools are introduced, the larger radial support members may be detached from the cannula and axially moved out of the trocar cannula.

Figure 1:
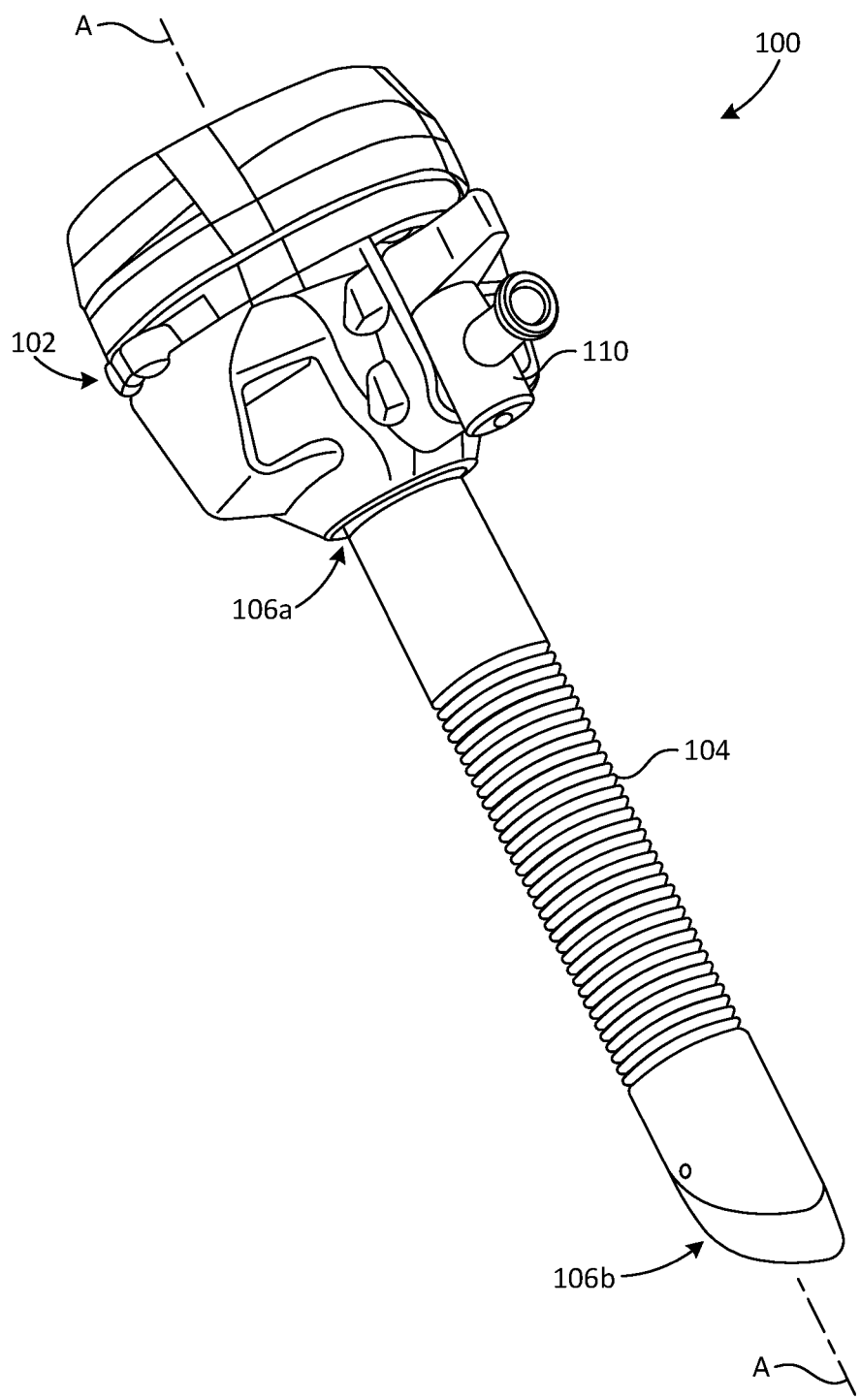
FIG. 1 is an isometric view of an example trocar assembly that may incorporate the principles of the present disclosure.

FIG. 1 is an isometric view of an example trocar assembly 100 that may incorporate the principles of the present disclosure. The depicted trocar assembly 100 is just one example trocar assembly that can suitably incorporate the principles of the present disclosure. Indeed, many alternative designs and configurations of the trocar assembly 100 may be employed, without departing from the scope of this disclosure.

As illustrated, the trocar assembly 100 includes a trocar housing 102 and a cannula 104, and the cannula 104 has a proximal end 106a and a distal end 106b. The cannula 104 is coupled to the trocar housing 102 at the proximal end 106a and extends distally therefrom. In some embodiments, the cannula 104 may comprise an integral extension of the trocar housing 102. In other embodiments, however, the trocar housing 102 and the cannula 104 may comprise two separate components that may be mated to one another. The trocar housing 102 and cannula 104 may be made of any rigid or semi-rigid material, such as a metal or a plastic.

The trocar assembly 100 may also include an insufflation valve 110 (e.g., a stopcock valve) coupled to the trocar housing 102 or forming an integral part thereof. The insufflation valve 110 is operable to introduce an insufflation fluid (e.g. carbon dioxide) through the trocar housing 102 and the cannula 104 and subsequently into an inner cavity (e.g., the abdomen) of a patient to elevate the interior walls of the inner cavity. While not shown, the trocar assembly 100 may also include an obturator extendable through the trocar assembly along a centerline A of the trocar assembly 100. When used, the obturator extends through the cannula 104 and out the distal end 106b to penetrate a patient's skin and thereby facilitate access to the abdominal cavity.

Figure 2:
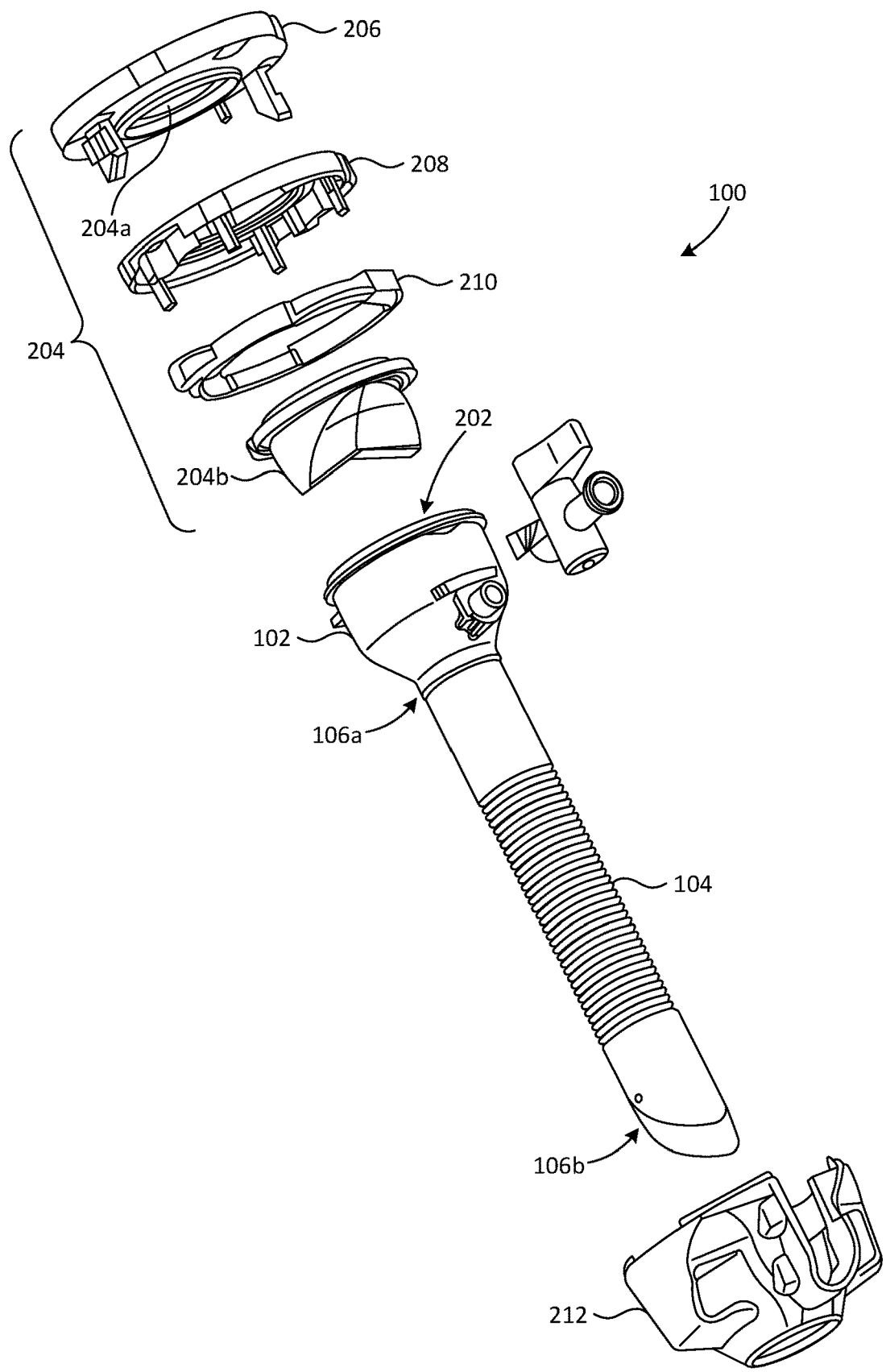
FIG. 2 is an exploded view of the trocar assembly of FIG. 1.

FIG. 2 is an exploded view of the trocar assembly 100 of FIG. 1. The trocar housing 102 provides and otherwise defines a working chamber 202 that communicates with a lumen defined within the cannula 104. The lumen is open-ended and extends between the proximal and distal ends 106a,b of the cannula 104.

The working chamber 202 is also open-ended and configured to at least partially receive a seal cartridge 204 that includes a first or "proximal" seal assembly 204a and a second or "distal" seal assembly 204b. The first and second seal assemblies 204a,b allow selective sealing of the working chamber 202 during operation. In at least one embodiment, as illustrated, the second seal assembly 204b may comprise a duckbill seal. While two seal assemblies 204a,b are depicted in FIG. 2, the seal cartridge 204 may alternatively include more or less than two seal assemblies, without departing from the scope of the disclosure.

The seal assemblies 204a,b may be made of an elastic or pliable material, and suitable elastic or pliable materials include, but are not limited to, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), silicone, ethylene vinyl acetate, nylon, vinyl, spandex, polyurethane, polyethylene, polypropylene, polyisoprene, or any combination thereof. Example seal cartridges are described in U.S. Pat. No. 8,771,307, the contents of which are hereby incorporated by reference.

The seal cartridge 204 may be assembled in a variety of ways. In the illustrated embodiment, for example, a crown ring 206 and a gasket ring 208 may be snap-fit together, and a gasket retainer ring 210 may be configured to secure an attachment between the gasket ring 208 and the trocar housing 102. A housing retainer 212 may then be extended about the exterior of the trocar housing 102 to secure the internal components to the trocar housing 102. These components may be made of any rigid or semi-rigid material, such as a metal or a plastic.

Figure 3:
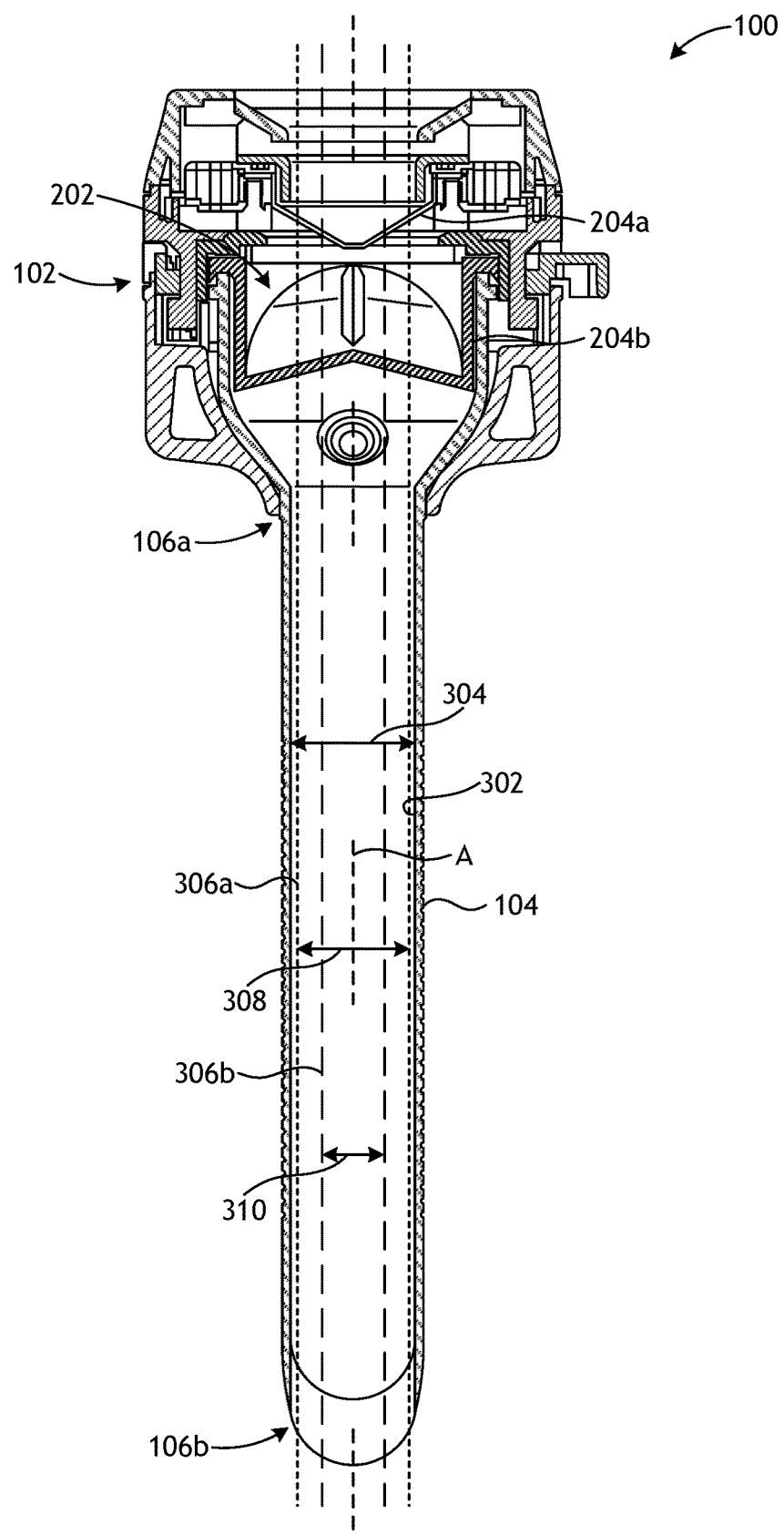
FIG. 3 is a cross-sectional side view of the trocar assembly of FIG. 1.

FIG. 3 is a cross-sectional side view of the trocar assembly 100. As illustrated, the cannula 104 defines and otherwise provides a lumen 302 that extends between the proximal and distal ends 106a,b and communicates with the working chamber 202 provided by the trocar housing 102. The lumen 302 exhibits an inner diameter 304 configured to receive surgical tools having an outer diameter equal to (i.e., slightly less than equal) or less than the inner diameter 304.

In at least one embodiment, the inner diameter 304 may be sized to receive a 12 mm surgical tool. In such embodiments, the trocar assembly 100 may be referred to and otherwise characterized as a "12 mm trocar," which is commonly used in robotic surgery to accommodate various 12 mm surgical tools, such as surgical staplers. In the illustrated embodiment, a first surgical tool 306a is depicted in dashed lines as extended through the trocar assembly 100 and projecting out each end. While not explicitly shown, as the first surgical tool 306a is extended into the trocar assembly 100, the first and second seal assemblies 204a,b are configured to deform and provide a sealed interface against the outer surface of the first surgical tool 306a.

The first surgical tool 306a exhibits an outer diameter 308 of approximately 12 mm, which is slightly smaller than the inner diameter 304 of the lumen 302. Accordingly, the first surgical tool 306a may be referred to as a "12 mm surgical tool" and the lumen 302 is sized to receive the first surgical tool 306a such that very little space (e.g., less than 1 mm) remains between the inner and outer diameters 304, 308. Consequently, the first surgical tool 306a is generally centered within the cannula 302 along the centerline A at all times, which tends to mitigate unwanted occurrences of deflection, oscillation, and vibration of the first surgical tool 306a.

At times, however, smaller surgical tools may need to be introduced into the trocar assembly 100 to perform additional procedures. In the illustrated embodiment, for example, a second surgical tool 306b is depicted in dashed lines as extended through the trocar assembly 100 and projecting out each end. Similar to the first surgical tool 306a, as the second surgical tool 306b is extended into the trocar assembly 100, the first and second seal assemblies 204a,b are configured to deform and provide a sealed interface against the outer surface of the second surgical tool 306b.

The second surgical tool 306b exhibits an outer diameter 310 that is smaller than the outer diameter 308 of the first surgical tool 306a, and smaller than the inner diameter 304 of the lumen 302. In some applications, for example, the outer diameter 310 may be approximately 8 mm. In such applications, the second surgical tool 306b may be referred to as an "8 mm surgical tool." Alternatively, the outer diameter 310 may be approximately 5 mm, and the second surgical tool 306b may instead be referred to as a "5 mm surgical tool."

Since the outer diameter 310 of the second surgical tool 306b is much smaller than the inner diameter 304 of the lumen 302, the second surgical tool 306b will rarely (if ever) be centered within the cannula 302 along the centerline A during operation. Rather, during operation the second surgical tool 306b will continuously be prone to deflection, oscillation in place, spring back oscillation, and vibration as the second surgical tool 306b is manipulated in various directions. As discussed above, such unintended "lost motion" or hysteresis is unacceptable to a surgeon, who expects fine control and precision from during robotic operations.

According to embodiments of the present disclosure, the trocar assembly 100 may incorporate a radial support assembly (not shown) arranged at or near the distal end 106b of the cannula 104. The radial support assembly may include a plurality of radial support members that extend radially inward to engage the outer surface of surgical tools extended within the cannula 104 and thereby help center the surgical tools within the cannula 104 and eliminate or significantly minimize unintended oscillation and vibration. In some embodiments, the radial support members may be radially compliant and therefore, able to accommodate varying diameters of surgical tools that may be used in the trocar assembly 100. In other embodiments, the radial support members may comprise keystones arranged side by side to form a ring within the cannula 104. Some of the radial support members extend inward to a first depth, while others extend inward to a second depth. This allows the larger radial support members to accommodate smaller-diameter surgical tools (e.g., the second surgical tool 306b), while the smaller radial support members radially support larger-diameter surgical tools (e.g., the first surgical tool 306a or larger tools). Moreover, the larger radial support members may be axially translatable and otherwise movable out of the cannula 104 when acted upon by larger-diameter surgical tools.

FIG. 4 depicts an example radial support assembly 402 that may be incorporated into the trocar assembly 100 of FIGS. 1-3, according to one or more embodiments of the present disclosure. As illustrated, the radial support assembly 402 may be positioned and otherwise arranged at or near the distal end 106b of the cannula 104. The radial support assembly 402 includes a plurality of radial support members 404 in the form of lugs, keys, or keystones. Each radial support member 404 is mounted to a corresponding support column 406 (two partially shown) and each extends radially inward from the corresponding support column 406 and toward the centerline A of the cannula 104. The support columns 406 extend axially between a first or upper cannula portion 408a and a second or lower cannula portion 408b and serve to operatively connect the upper and lower cannula portions 408a,b.

While only four radial support members 404 (and corresponding support columns 406) are depicted in FIG. 4, more or less than four may be employed without departing from the scope of the disclosure. Moreover, in some embodiments, as illustrated, the radial support members 404 may be equidistantly spaced from each other about the circumference of the cannula 104. Embodiments with two radial support members 404, for example, may be angularly offset from each other by approximately 180°, embodiments with three radial support members 404 may be angularly offset from each other by approximately 120°, and embodiments with four radial support members 404 may be angularly offset from each other by approximately 90°. In other embodiments, however, the radial support members 404 may alternatively be non-equidistantly spaced from each other about the circumference of the cannula 104 and otherwise spaced in any desired angular configuration.

The radial support members 404 may be made of a variety of rigid or semi-rigid materials. In some embodiments, for instance, the radial support members 404 may be made of the same material used to manufacture the cannula 104, such as, but not limited to, stainless steel, spring steel, plastic, or nylon. In other embodiments, the radial support members 404 may be made of a material that is dissimilar to that of the cannula 104 such as, but not limited to, vinyl, polyurethane, polyethylene, polypropylene, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), a fluoropolymer (e.g., Polytetrafluoroethylene), polyether ether keytone (PEEK), silicone, nylon, or any combination thereof.

FIGS. 5A and 5B show various views of the component parts of the radial support assembly 402 of FIG. 4. More specifically, FIG. 5A shows the radial support assembly 402 of FIG. 4 without the radial support members 404, according to one or more embodiments. As illustrated, a window or gap 502 is defined in the cannula 104 near the distal end 106b and bifurcates the cannula 104 into the upper and lower cannula portions 408a,b. As indicated above, the upper and lower cannula portions 408a,b are coupled and otherwise connected with the plurality of support columns 406 extending therebetween.

FIG. 5B is an exploded view of a portion of the radial support assembly 402 of FIG. 4. More particularly, FIG. 5B shows example assembly of one radial support member 404 and a corresponding support column 406, according to one or more embodiments. Assembly of the illustrated radial support member 404 and support column 406 is representative of assembly of any of the radial support members 404 and corresponding support columns 406 of FIG. 4. Accordingly, the following assembly steps may be undertaken for all four combinations of radial support members 404 and support columns 406 shown in the embodiment of FIG. 4.

As illustrated, the radial support member 404 defines or otherwise provides a longitudinal slot 504 configured (sized) to receive the corresponding support column 406, which mounts the radial support member 404 thereto. Moreover, the radial support member 404 may define a pocket 506 contiguous with the longitudinal slot 504 and configured to receive and seat a biasing device 508 that interposes the radial support member 404 and the support column 406. In the illustrated embodiment, the biasing device 508 is a compression spring, but could alternatively be any other mechanism or device that provides a biasing force between the radial support member 404 and the support column 406.

To assemble the combination, the biasing device 508 is first received into the pocket 506, and the radial support member 404 is then fitted (mounted) onto the support column 406 by receiving the support column 406 within the longitudinal slot 504. The axial height of the radial support member 404 is less than the height of the gap 502 (FIG. 5B); i.e., distance between the upper and lower cannula portions 408a,b (FIGS. 4 and 5A). Accordingly, the radial support member 404 is able to fit between the upper and lower cannula portions 408a,b. During operation, the biasing device 508 engages and pushes against the support column 406 and continuously urges the radial support member 404 toward the centerline A (FIG. 4) of the cannula 104 (FIGS. 4 and 5A).

The radial support member 404 may also provide and otherwise define an inner surface 510 configured to engage the outer radial surface of a surgical tool (not shown) extended within the cannula 104 (FIGS. 4 and 5A) and through the radial support assembly 402. In some embodiments, the inner surface 510 may be arcuate (curved) to enable the support member 404 to cradle the outer radial surface of a surgical tool extended through (within) the radial support assembly 402. In other embodiments, however, the inner surface 510 may instead be flat, without departing from the scope of the disclosure.

In some embodiments, the inner surface 510 may also provide or otherwise transition into a beveled surface 512. The beveled surface 512 may prove advantageous in helping the radial support assembly 402 receive surgical tools (not shown) of varying diameters. More specifically, a surgical tool introduced into the cannula 104 (FIGS. 4 and 5A) and advanced toward the radial support assembly 402 may be configured to first slidingly engage the beveled surface 512. As the surgical tool engages the beveled surface 512 and advances through the radial support assembly 402, the radial support member 404 will be urged radially outward and the biasing device 508 will correspondingly compress to accommodate the outer diameter of the surgical tool. Once the surgical tool is removed, the biasing device 508 is allowed to expand and force the radial support member 404 back toward the centerline A (FIG. 4).

Figure 6A:
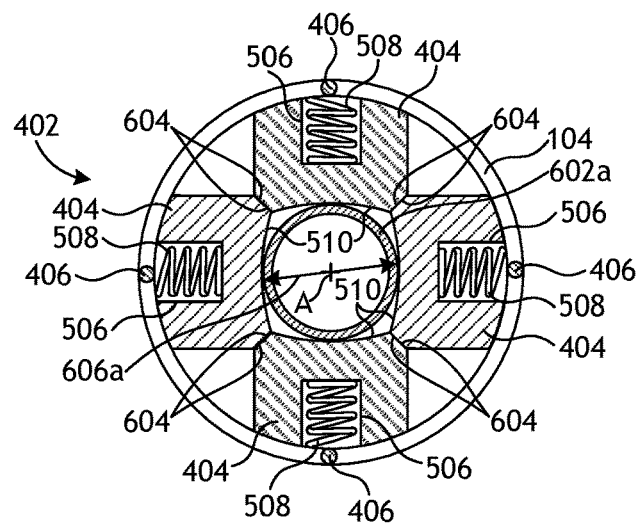
FIGS. 6A-6C are cross-sectional end views of the radial support assembly of FIG. 4 as taken along the line indicated in FIG. 4.
Figure 6B:
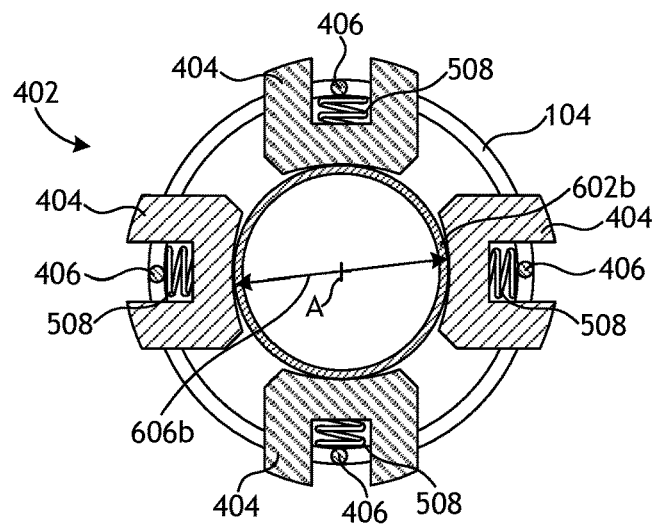
Figure 6C:
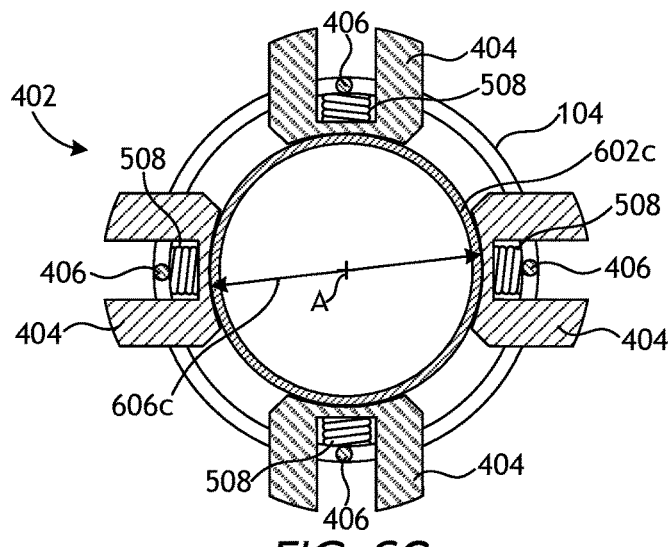

FIGS. 6A-6C are cross-sectional end views of the radial support assembly 402 as taken along the line indicated in FIG. 4. FIGS. 6A-6C also depict progressive operation of the radial support assembly 402 while accommodating surgical tools of varying sizes (diameters). When accommodating surgical tools of varying sizes, the radial support assembly 402 may be configured to move between a relaxed position, as shown in FIG. 6A, to various degrees of biased positions, as shown in FIGS. 6B and 6C.

In FIG. 6A, a first surgical tool 602*a* is depicted as received within the cannula 104 and simultaneously within the radial support assembly 402 coupled to the cannula 104. The biasing device 508 received within the pocket 506 of each radial support member 404 acts on a corresponding support column 406 and urges the corresponding radial support member 404 radially inward and toward the centerline A. The spring force of the biasing devices 508 urges the radial support members 404 radially inward until the inner surface 510 of each radial support member 404 engages or comes into close contact with the outer radial surface of the first surgical tool 602*a*. In embodiments where the inner surface 510 is arcuate, as illustrated, the inner surface 510 may cradle the outer radial surface of the surgical tool 602*a*. The radial support members 404 operate to generally center the first surgical tool 602*a* within the cannula 104, and thereby eliminate or significantly minimize unintended oscillation and/or vibration of the first surgical tool 602*a*.

In some embodiments, as illustrated, each radial support member 404 may have or define beveled edges or corners 604. When the radial support assembly 402 is in the relaxed position, as shown in FIG. 6A, the beveled corners 604 of each radial support member 404 may be configured (angled) to engage opposing beveled corners 604 of angularly adjacent radial support members 404. Moreover, the first surgical tool 602*a* may have a first diameter 606*a* small enough to allow the radial support assembly 402 to operate in the relaxed position where the beveled corners 604 come into engagement with one another.

FIG. 6B shows a second surgical tool 602*b* received within the cannula 104 and simultaneously within the radial support assembly 402. The second surgical tool 602*b* has a second diameter 606*b* larger than the first diameter 606*a* (FIG. 6A) of the first surgical tool 602*a* (FIG. 6A). Consequently, when the second surgical tool 602*b* is received within the radial support assembly 402, the radial support assembly 402 transitions (moves) from the relaxed position of FIG. 6A to a first biased position. The larger-diameter second surgical tool 602*b* acts on and urges the radial support members 404 radially outward and away from the centerline A, while simultaneously compressing the biasing devices 508 against the support columns 406 to accommodate the larger size.

FIG. 6C shows a third surgical tool 602*c* received within the cannula 104 and simultaneously within the radial support assembly 402. The third surgical tool 602*c* has a third diameter 606*c* larger than the second diameter 606*b* (FIG. 6B) of the second surgical tool 602*b* (FIG. 6B), which forces the radial support assembly 402 to transition (move) to a second biased position. The larger-diameter third surgical tool 602*c* acts on and urges the radial support members 404 even further radially outward and away from the centerline A, while simultaneously compressing the biasing devices 508 against the support columns 406 to accommodate the larger size.

The radial support members 404 in FIGS. 6B and 6C generally center the second and third surgical tools 602*b, c* within the cannula 104, and thereby eliminate or significantly minimize unintended oscillation and/or vibration thereof. Once the second and third surgical tools 602*b, c* are removed, the biasing devices 508 are allowed to expand and force the radial support members 404 back toward the centerline A and to the relaxed position once more.

In some embodiments, the radial support members 404 may be lubricious (e.g., slippery or slick), which may advantageously reduce the drag force against the surgical tools passing through the cannula 104. In some embodiments, for example, the radial support members 404 may be made of a lubricious material, such as nylon, polished metal, or a smooth plastic. In other embodiments, however, the radial support members 404 may be coated with a lubricious substance or material such as, but not limited to, oil, graphite, TEFLON™, silicone, and any combination thereof.

Figure 7A:
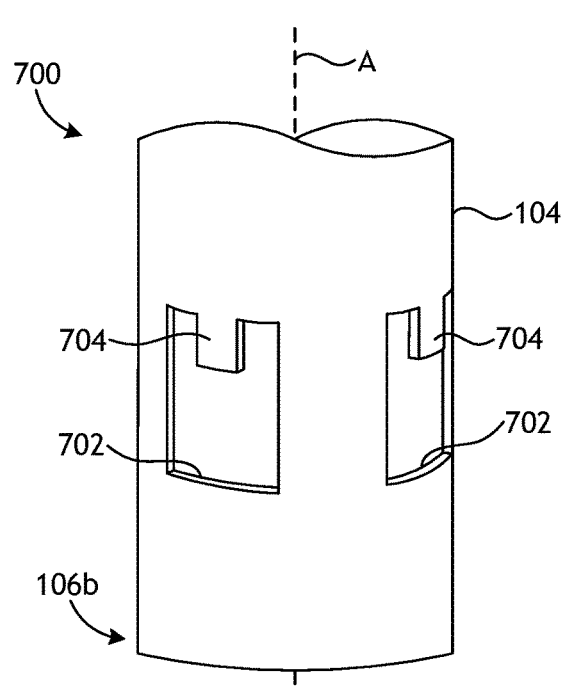
FIGS. 7A and 7B show an alternative embodiment of another example radial support assembly.
Figure 7B:
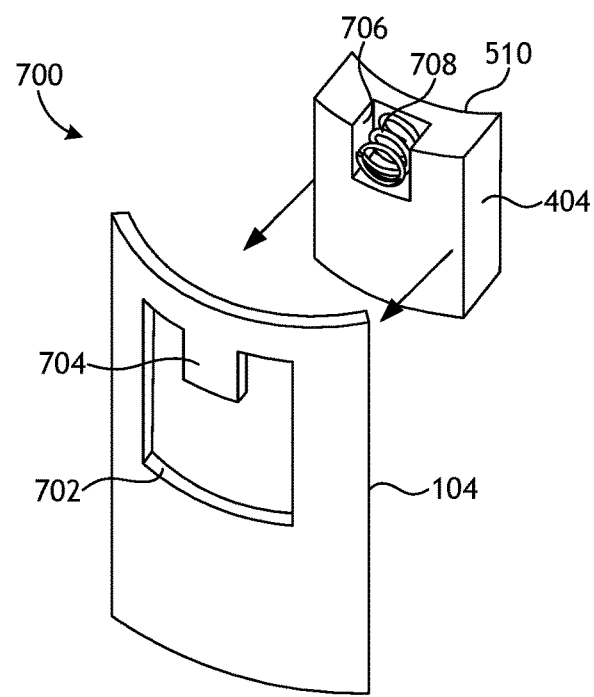

FIGS. 7A and 7B show an alternative embodiment of another example radial support assembly 700, according to one or more embodiments. As shown in FIG. 7A, the radial support assembly 700 includes a plurality of windows 702 (two shown) defined in the cannula 104 at or near the distal end 106*b* thereof. While only two windows 702 are shown in FIG. 7A, more than two windows 702 (e.g., four) may be employed, without departing from the scope of the disclosure. FIG. 7B is an exploded view of a portion of the radial support assembly 700 and depicts example assembly of one radial support member 404 to a corresponding window 702, according to one or more embodiments. As illustrated, the window 702 may be shaped and otherwise configured to receive and seat the radial support member 404.

While only one combination radial support member 404 and corresponding window 702 are shown in FIG. 7B, it will be appreciated that a plurality of radial support members 404 and corresponding windows 702 may form part of the radial support assembly 700. Consequently, assembly of the illustrated radial support member 404 and corresponding window 702 in FIG. 7B is representative of assembly of any of the radial support members 404 and corresponding windows 702 that may be included in the radial support assembly 700. Accordingly, the following assembly steps may be undertaken for all combinations of radial support members 404 and windows 702 for the radial support assembly 700.

In the illustrated embodiment, each window 702 may have a generally square or rectangular shape (profile) with a tab 704 extending inward from one side. Accordingly, each radial support member 404 may have a generally square or rectangular shape. In other embodiments, however, the window(s) 702 and the radial support member(s) 404 may exhibit any shape or configuration, including polygonal, circular, ovular, or irregular shapes, without departing from the scope of the disclosure.

The radial support member 404 may also define or otherwise provide a pocket 706 configured to align with the tab 704. The pocket 706 may be sized to receive and seat a biasing device 708 that interposes the radial support member 404 and the tab 704. The biasing device 708 may be the same as or similar to the biasing device 508 of FIG. 5B.

To assemble the combination, the biasing device 708 is first received into the pocket 706, and the radial support member 404 is then fitted or received within the window 702. During operation, the biasing device 708 engages the tab 704 and continuously urges the radial support member 404 toward the centerline A (FIG. 7A) of the cannula 104. In some embodiments, the biasing device 708 may be coupled to the radial support member 404 and the tab 704, and thereby helps maintain the radial support member 404 seated within the window 702.

In some embodiments, as illustrated, the inner surface 510 of the radial support members 404 may be arcuate to engage and cradle the outer radial surface of a surgical tool (not shown). The surgical tool will urge the radial support member 404 radially outward and the biasing device 708 will correspondingly compress to accommodate the outer diameter of the surgical tool. Once the surgical tool is removed, the biasing device 708 is allowed to expand and force the radial support member 404 back toward the centerline A (FIG. 7A).

Figure 8A:
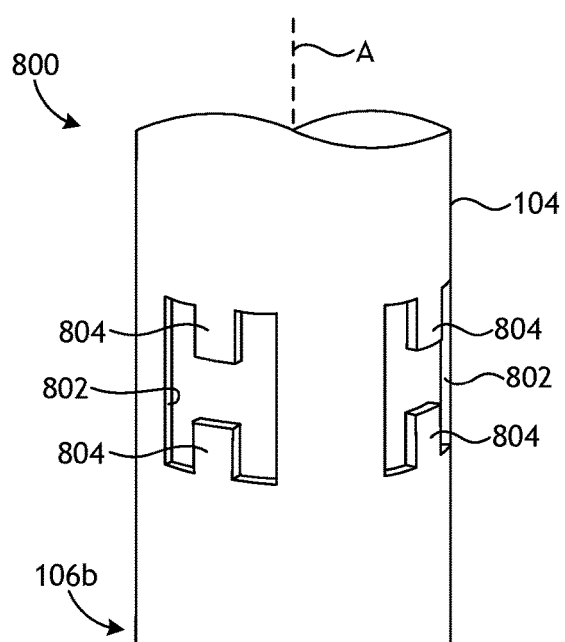
FIGS. 8A and 8B show another alternative embodiment of another example radial support assembly.
Figure 8B:
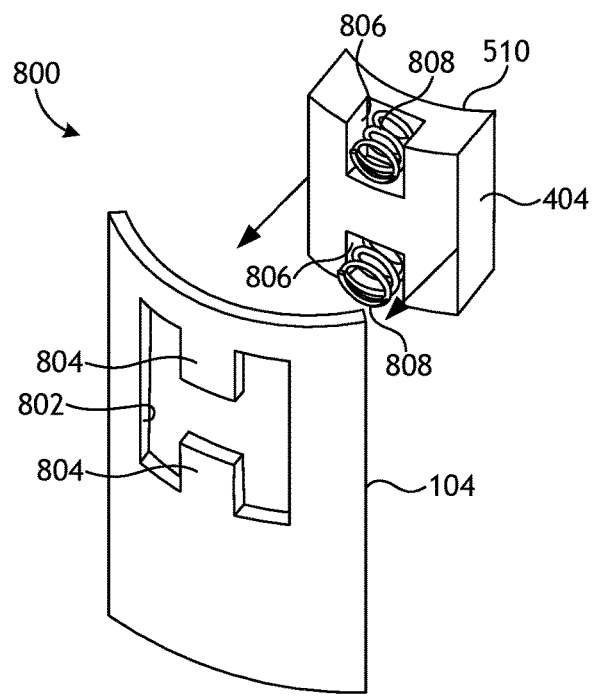

FIGS. 8A and 8B show another alternative embodiment of another example radial support assembly 800, according to one or more embodiments. The radial support assembly 800 may be similar in some respects to the radial support assembly 700 of FIGS. 7A and 7B and therefore may be best understood with reference thereto. Similar to the radial support assembly 700 of FIGS. 7A and 7B, the radial support assembly 800 includes a plurality of windows 802 (two shown in (FIG. 8A) defined in the cannula 104 at or near the distal end 106b thereof. Moreover, each window 802 may be shaped and otherwise configured to receive and seat a corresponding radial support member 404, as shown in FIG. 8B, which is an exploded view of a portion of the radial support assembly 800 and depicts example assembly of one radial support member 404 to a corresponding window 802.

Unlike the windows 702 of FIGS. 7A and 7B, however, each window 802 may have two or more tabs 804. In the illustrated embodiment, the tabs 804 extend inward from opposing sides of the window 802, but could alternatively be arranged at other locations, without departing from the scope of the disclosure. Accordingly, each window 802 may be in the general shape of the letter "H". As shown in FIG. 8B, each radial support member 404 may be configured or shaped to be received by the corresponding window 802. Accordingly, each radial support member 404 may have a generally square or rectangular shape and may further define or otherwise provide two pockets 806, each configured to align with a corresponding tab 804. Moreover, each pocket 806 may be sized to receive and seat an individual biasing device 808 that interposes the radial support member 404 and the corresponding tab 804. The biasing devices 808 may be the same as or similar to the biasing device 508 of FIG. 5B.

To assemble the combination, the biasing devices 808 are first received into the pockets 806, and the radial support member 404 is then fitted or received within the window 802. During operation, the biasing devices 808 engage the corresponding tabs 804 and continuously urge the radial support member 404 toward the centerline A (FIG. 8A) of the cannula 104. In some embodiments, as illustrated, the inner surface 510 of the radial support members 404 may be arcuate to engage and cradle the outer radial surface of a surgical tool (not shown). The surgical tool will urge the radial support members 404 radially outward and the biasing devices 808 will correspondingly compress to accommodate the outer diameter of the surgical tool. Once the surgical tool is removed, the biasing devices 808 are allowed to expand and force the radial support member 404 back toward the centerline A (FIG. 8A).

Figure 9A:
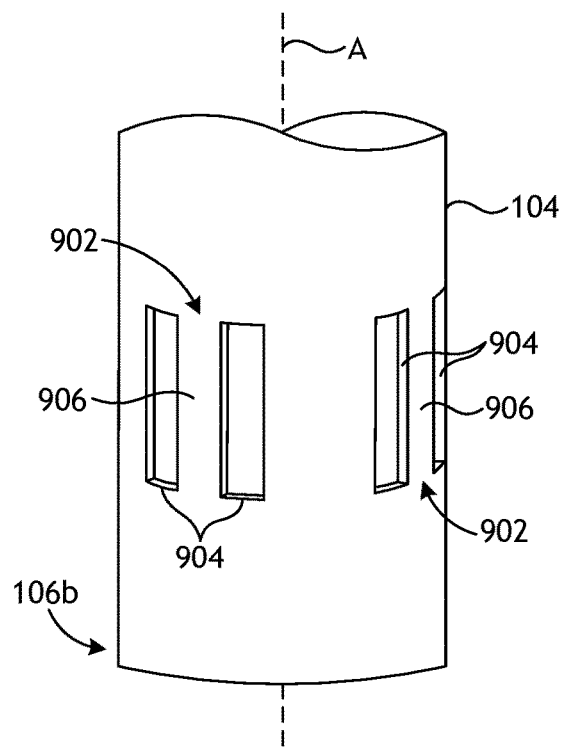
FIGS. 9A and 9B show another alternative embodiment of another example radial support assembly.
Figure 9B:
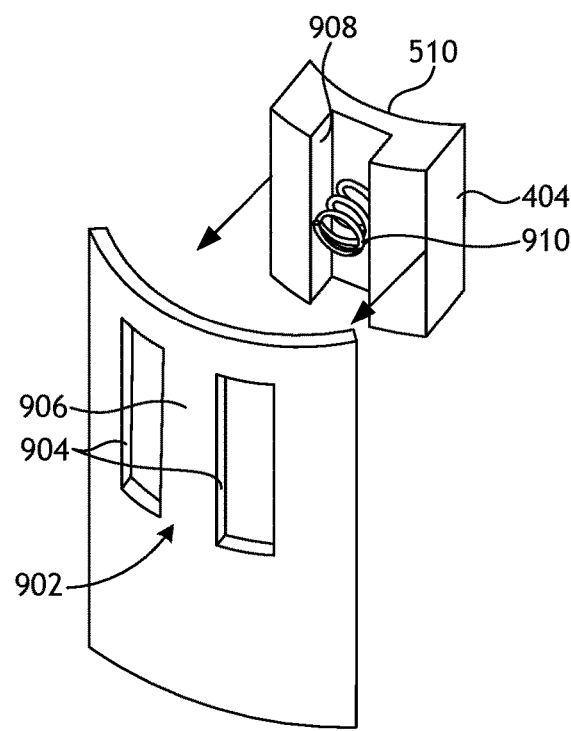

FIGS. 9A and 9B show yet another alternative embodiment of another example radial support assembly 900, according to one or more embodiments. The radial support assembly 900 may be similar in some respects to the radial support assemblies 700 and 800 of FIGS. 7A-7B and 8A-8B, respectively, and therefore may be best understood with reference thereto. Similar to the radial support assemblies 700 and 800, the radial support assembly 900 includes a plurality of windows 902 defined in the cannula 104 at or near the distal end 106b thereof, as shown in FIG. 9A, and each window 902 may be shaped and otherwise configured to receive and seat a corresponding radial support member 404, as shown in FIG. 9B.

Unlike the windows 702, 802 of FIGS. 7A-7B and 8A-8B, respectively, however, each window 902 may comprise two longitudinal slots 904 that run parallel to one another and have a central portion 906 interposing the slots 904. As shown in FIG. 9B, each radial support member 404 may be configured or shaped to be received by the corresponding window 902. Accordingly, each radial support member 404 may define or otherwise provide a pocket 908 configured to align with the central portion 906. Moreover, the pocket 908 may be sized to receive and seat a biasing device 910 that interposes the radial support member 404 and the central portion 906. The biasing device 910 may be the same as or similar to the biasing device 508 of FIG. 5B. In some embodiments, more than one biasing device 508 may be arranged within the pocket 908.

To assemble the combination, the biasing device 910 is first received into the pocket 908, and the radial support member 404 is then fitted or received within the window 902. During operation, the biasing device 910 engages the inner wall of the central portion 906 and continuously urges the radial support member 404 toward the centerline A (FIG. 9A) of the cannula 104. In some embodiments, as illustrated, the inner surface 510 of the radial support members 404 may be arcuate to engage and cradle the outer radial surface of a surgical tool (not shown). The surgical tool will urge the radial support members 404 radially outward and the biasing device 910 will correspondingly compress to accommodate the outer diameter of the surgical tool. Once the surgical tool is removed, the biasing device 910 is allowed to expand once more and force the radial support member 404 back toward the centerline A (FIG. 9A).

Figure 10A:
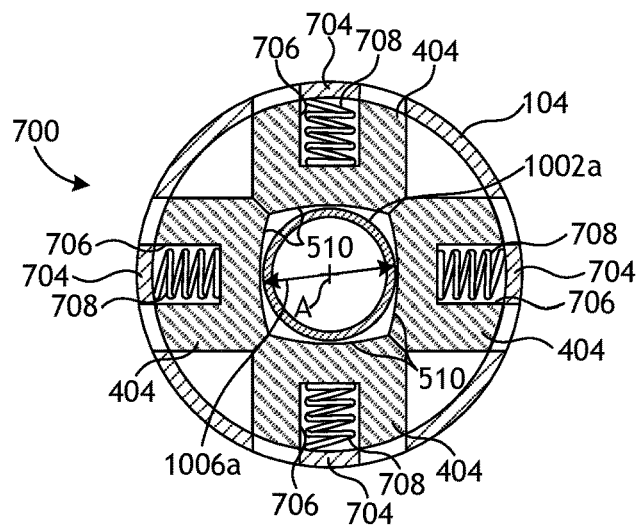
FIGS. 10A-10C are cross-sectional end views of the radial support assembly of FIGS. 7A-7B showing progressive operation.
Figure 10B:
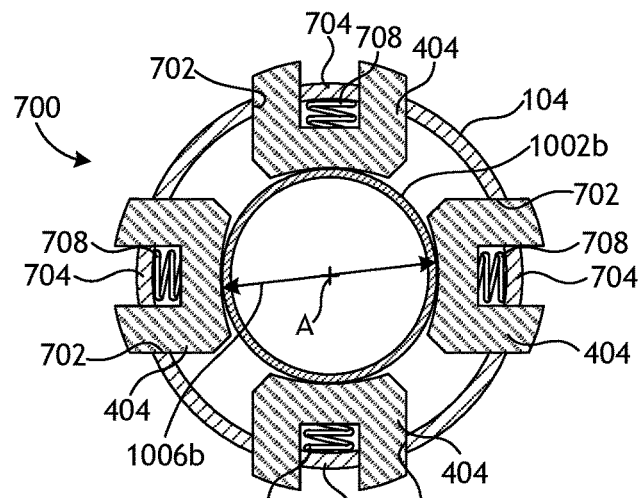
Figure 10C:
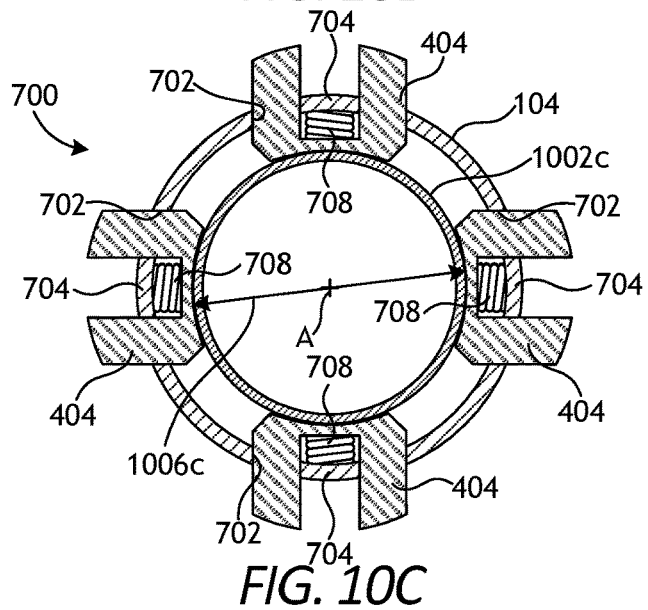

FIGS. 10A-10C are cross-sectional end views of the radial support assembly 700 of FIGS. 7A-7B. More particularly, FIGS. 10A-10C depict progressive operation of the radial support assembly 700 while accommodating surgical tools of varying sizes (diameters). When accommodating surgical tools of varying sizes (diameters), the radial support assembly 700 may be configured to move between a relaxed position, as shown in FIG. 10A, to various degrees of biased positions, as shown in FIGS. 10B and 10C. As will be appreciated, the operational specifics shown in FIGS. 10A-10C could equally be applied to either of the radial support assemblies 800 or 900 of FIGS. 8A-8B and 9A-9B, respectively. Accordingly, the following operational description may be equally applicable to operating either of the radial support assemblies 800, 900.

In FIG. 10A, a first surgical tool 1002*a* is depicted as received within the cannula 104 and simultaneously within the radial support assembly 700 arranged on the cannula 104. The biasing device 708 received within the pocket 706 of each radial support member 404 acts on a corresponding tab 704 and urges the corresponding radial support member 404 radially inward and toward the centerline A. The spring force of the biasing devices 708 urges the radial support members 404 radially inward until the inner surface 510 of each radial support member 404 engages or comes into close contact with the outer radial surface of the first surgical tool 1002*a*. The first surgical tool 1002*a* may have a first diameter 1006*a* small enough to allow the radial support assembly 700 to operate in the relaxed position. The radial support members 404 operate to generally center the first surgical tool 1002*a* within the cannula 104, and thereby eliminate or significantly minimize unintended oscillation and/or vibration of the first surgical tool 1002*a*.

FIG. 10B shows a second surgical tool 1002*b* received within the cannula 104 and simultaneously within the radial support assembly 700. The second surgical tool 1002*b* has a second diameter 1006*b* larger than the first diameter 1006*a* (FIG. 10A) of the first surgical tool 1002*a* (FIG. 10A). Consequently, the radial support assembly 700 is moved from the relaxed position of FIG. 10A to a first biased position. The larger-diameter second surgical tool 1002*b* acts on and urges the radial support members 404 radially outward through the windows 702 and away from the centerline A, while simultaneously compressing the biasing devices 708 against the tabs 704 to accommodate the larger size.

The radial support members 404 generally center the second surgical tool 1002*b* within the cannula 104, and thereby eliminate or significantly minimize unintended oscillation and/or vibration of the second surgical tool 1002*b*. Once the second surgical tool 1002*b* is removed, the biasing devices 708 are allowed to expand and force the radial support members 404 back toward the centerline A and to the relaxed position once more.

FIG. 10C shows a third surgical tool 1002*c* received within the cannula 104 and simultaneously within the radial support assembly 700. The third surgical tool 1002*c* has a third diameter 1006*c* larger than the second diameter 1006*b* (FIG. 10B) of the second surgical tool 1002*b* (FIG. 10B). Consequently, the radial support assembly 700 is moved to a second biased position. The larger-diameter third surgical tool 1002*c* acts on and urges the radial support members 404 further radially outward through the corresponding windows 702 and away from the centerline A, while simultaneously compressing the biasing devices 708 against the tabs 704 to accommodate the larger size.

The radial support members 404 generally center the third surgical tool 1002*c* within the cannula 104, and thereby eliminate or significantly minimize unintended oscillation and/or vibration of the third surgical tool 1002*c*. Once the third surgical tool 1002*c* is removed, the biasing devices 708 are allowed to expand and force the radial support members 404 back toward the centerline A and to the relaxed position once more.

Figure 11A:
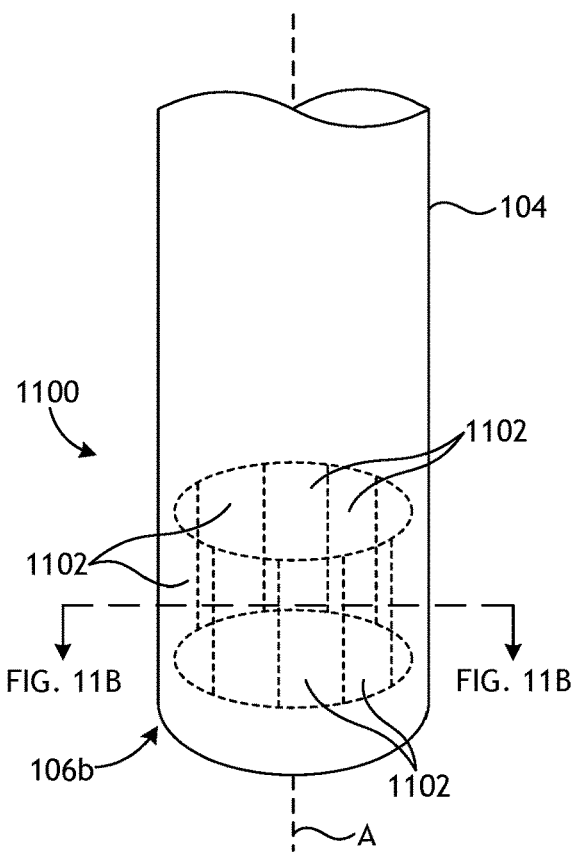
FIG. 11A depicts another example radial support assembly that may be incorporated into the trocar assembly of FIGS. 1-3.

FIG. 11A depicts another example radial support assembly 1100 (shown in dashed lines) that may be incorporated into the trocar assembly 100 of FIGS. 1-3, according to one or more additional embodiments. As illustrated, the radial support assembly 1100 may be arranged within the cannula 104 at or near the distal end 106*b*. The radial support assembly 1100 includes a plurality of radial support members 1102 (also shown in dashed lines) arranged side by side to form a ring within the cannula 104. Each radial support assembly 1100 extends radially inward toward the centerline A of the cannula 104.

Figure 11B:
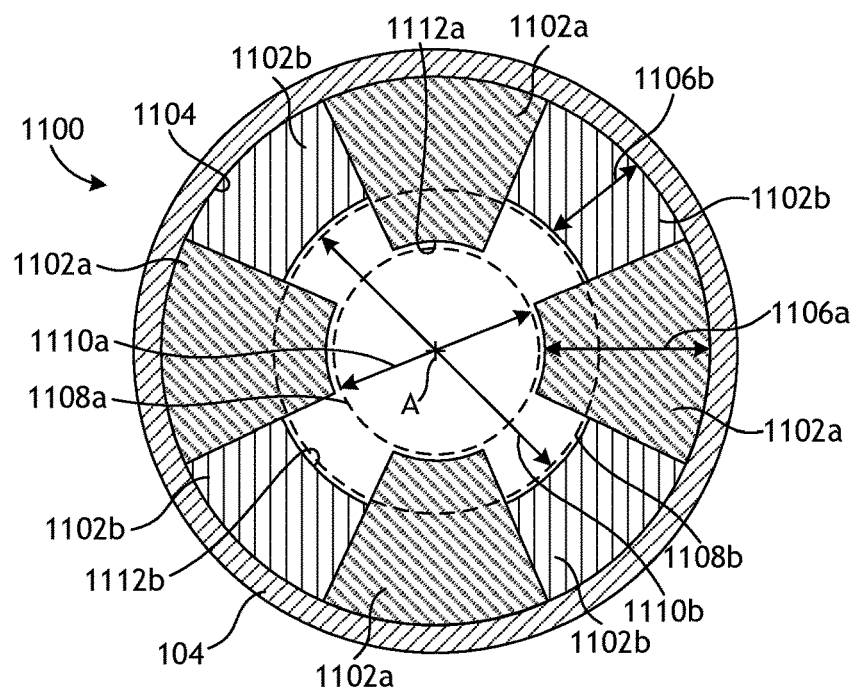
FIG. 11B is a cross-sectional end view of the radial support assembly of FIG. 11A as taken along the line indicated in FIG. 11A.

FIG. 11B is a cross-sectional end view of the radial support assembly 1100 as taken along the line indicated in FIG. 11A. As illustrated, the radial support members are provided in a first plurality of radial support members 1102*a* and a second plurality of radial support member 1102*b*, where each radial support member 1102*a,b* is in the general shape or form of a keystone. In the illustrated embodiment, the radial support members 1102*a,b* are arranged side-by-side within the cannula 104 and in the general shape of a ring, and the first and second pluralities of radial support members 1102*a,b* alternate about the inner circumference of the cannula 104. While depicted as alternating in a one-to-one pattern, the radial support members 1102*a,b* may alternatively alternate in a different pattern, such as one-to-two, two-to-two, etc., without departing from the scope of the disclosure. Moreover, while only two pluralities of radial support members 1102*a,b* are shown in FIG. 11B, it will be appreciated that more than two pluralities may be employed.

The first and second pluralities of radial support members 1102*a,b* may be secured to the cannula 104 in a variety of ways. In some embodiments, for example, the radial support members 1102*a,b* may be releasably attached to an inner radial surface 1104 of the cannula 104. In such embodiments, the radial support members 1102*a,b* may be secured to the inner radial surface 1104 with a releasable attachment that includes, but is not limited to, an adhesive, welding, brazing, a snap fit, a collet configuration, one or more shearable devices (e.g., shear pins, shear screws, etc.), or any combination thereof. The releasable attachment may be configured to fail upon the radial support members 1102*a,b* assuming a predetermined axial load, as discussed herein. In other embodiments, a breakaway gate may support the radial support members 1102*a,b* within the cannula 104 and the breakaway gate may also be configured to fail upon the radial support members 1102*a,b* assuming a predetermined axial load.

When the radial support assembly 1100 is assembled within the cannula 104, the first radial support members 1102*a* extend from the inner radial surface 1104 toward the centerline A to a first radial depth 1106*a*, and the of the second radial support members 1102*b* extend from the inner radial surface 1104 toward the centerline A to a second radial depth 1106*b*. As illustrated, the magnitude of the second radial depth 1106*b* is smaller than the magnitude of the first radial depth 1106*a*. The first radial support members 1102*a* may be configured to radially support a first surgical tool 1108*a* (shown in dashed lines) introduced into the cannula 104. In contrast, the second radial support members 1102*b* may be configured to radially support a second surgical tool 1108*b* (shown in dashed lines) 1110*a* when introduced into the cannula 104.

The first surgical tool 1108*a* may have a first diameter 1110*a*, and the second surgical tool 1108*b* may have a second diameter 1110*b* that is larger than the first diameter 1110*a*. In some embodiments, the first diameter 1110*a* may be approximately 5 mm and the second diameter 1110*b* may be approximately 8 mm. In such embodiments, the first surgical tool 1108*a* may be referred to as a "5 mm surgical tool" and the second surgical tool 1108*b* may be referred to as an "8 mm surgical tool."

In example operation, when the first surgical tool 1108a is introduced into the cannula 104 and extended through the radial support assembly 1100, an inner surface 1112a of each first radial support member 1102a engages or comes into close contact with the outer radial surface of the first surgical tool 1108a. In some embodiments, as illustrated, the inner surface 1112a may be arcuate and therefore capable of cradling the outer radial surface of the first surgical tool 1108a. The first radial support members 1102a operate to generally center the first surgical tool 1108a within the cannula 104, and thereby eliminate or significantly minimize unintended oscillation and/or vibration of the first surgical tool 1108a.

In contrast, when the second surgical tool 1108b is introduced into the cannula 104 and extended through the radial support assembly 1100, the second surgical tool 1108b will axially engage the first radial support members 1102a since the second diameter 1110b overlaps the first radial depth 1106a of the first radial support members 1102a. To advance the second surgical tool 1108b further distally, the first radial support members 1102a will have to be disengaged from the cannula 104 and forced distally. This can be accomplished by placing an axial load on the first radial support members 1102a with the second surgical tool 1108b in the distal direction until the first radial support members 1102a disengage (release) from the cannula 104.

Once disengaged from the cannula 104, the first radial support members 1102a may be pushed distally as the second surgical tool 1108b advances further in the distal direction. An inner surface 1112b of each second radial support member 1102b may then engage or come into close contact with the outer radial surface of the second surgical tool 1108b. In some embodiments, as illustrated, the inner surface 1112b may be arcuate and therefore capable of cradling the outer radial surface of the second surgical tool 1108b. The second radial support members 1102b operate to generally center the second surgical tool 1108b within the cannula 104, and thereby eliminate or significantly minimize unintended oscillation and/or vibration of the first surgical tool 602a.

Figure 11C:
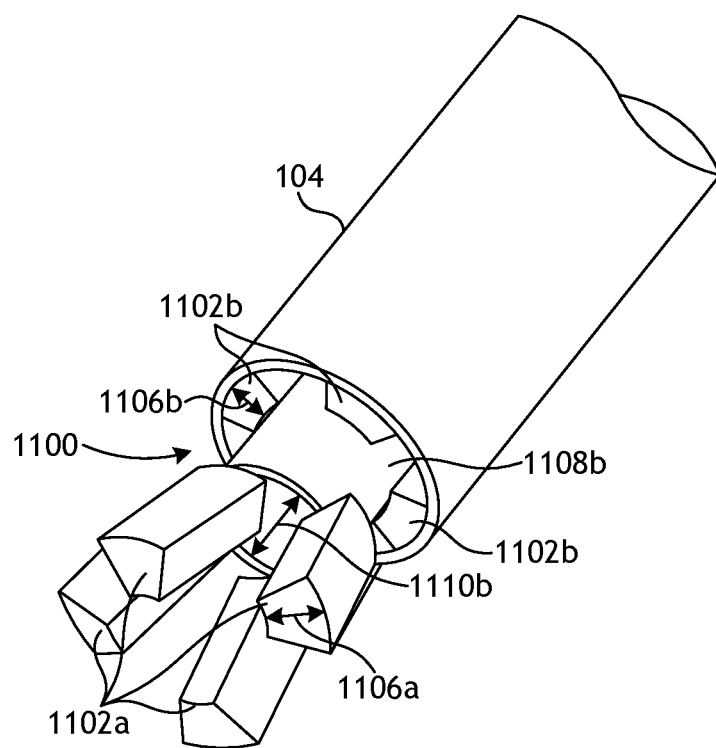
FIG. 11C is an isometric view of the radial support assembly of FIG. 11A depicting example operation.

FIG. 11C is an isometric view of the radial support assembly 1100 depicting example operation, according to one or more embodiments. More specifically, FIG. 11C depicts the second surgical tool 1108b extending through the cannula 104 and the radial support assembly 1100. Since the second diameter 1110b overlaps the first radial depth 1106a of the first radial support members 1102a, the second surgical tool 1108b will engage and force the first radial support members 1102a to detach from the cannula 104 as the second surgical tool 1108b advances distally. Once disengaged from the cannula 104, the first radial support members 1102a may be pushed out the bottom of the cannula 104 as the second surgical tool 1108b advances further in the distal direction.

In some embodiments, a third surgical tool (not shown) having a diameter greater than the first or second diameters 1110a,b (FIG. 11B) may be subsequently introduced into the cannula 104 and extended through the radial support assembly 1100. The diameter of the third surgical tool may be, for example, 12 mm, and the third surgical tool may therefore be referred to as a 12 mm surgical tool. In such embodiments, the third surgical tool will engage the second radial support members 1102b since the third diameter would overlap the second radial depth 1106b of the second radial support members 1102b. To advance the third surgical tool further distally, the second radial support members 1102b would have to be disengaged from the cannula 104. This can be accomplished by placing an axial load on the second radial support members 1102b with the third surgical tool in the distal direction until the second radial support members 1102b disengage from the cannula 104. Once disengaged from the cannula 104, the second radial support members 1102b may be pushed out the bottom of the cannula 104 as the third surgical tool advances further in the distal direction.

Since the first and second pluralities of radial support members 1102a,b may be configured to be detached and pushed out of the cannula 104, the radial support members 1102a,b may be discharged into an internal body cavity of a patient. Accordingly, in some embodiments, the first and second pluralities of radial support members 1102a,b may be made of a biodegradable material. In one or more embodiments, for example, the first and second pluralities of radial support members 1102a,b may be made of poly (glycolic acid) (PGA) or polylactic acid (PLA), which are biodegradable substances safe for medical use. As a result, the first and second pluralities of radial support members 1102a,b may be discharged from the cannula 104 and left in the internal body cavity of the patient to safely dissolve over time, according to some embodiments.

Figure 12:
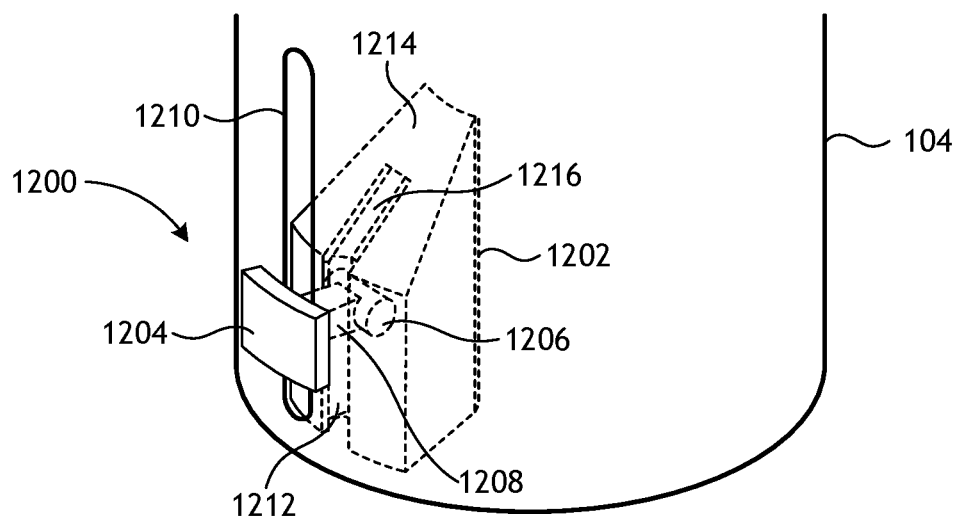
FIG. 12 depicts an example retention sled.

FIG. 12 depicts an example retention sled 1200 that may be used to movably attach a radial support member 1202 to the cannula 104, according to one or more embodiments. The radial support member 1202 may comprise any of the radial support members 1102a,b of FIG. 11B or 11C. Consequently, the retention sled 1200 may be used and otherwise incorporated into the radial support assembly 1100 of FIGS. 11A-11C. While only one retention sled 1200 and corresponding radial support member 1202 are depicted in FIG. 12, it will be appreciated that several combinations of retention sleds and radial support members may be employed to form a complete radial support assembly; i.e., a ring disposed within the cannula 104.

The retention sled 1200 may prove advantageous in preventing the radial support member 1202 from falling into a body cavity of a patient when forced out of the cannula 104. Moreover, in some embodiments, the retention sled 1200 may allow the radial support member 1202 to be reversible and otherwise re-positioned back within the cannula 104 for subsequent use.

As illustrated, the retention sled 1200 includes a slider 1204, a head 1206, and an arm 1208 that extends between the slider 1204 and the head 1206. The slider 1204 is generally positioned on the exterior of the cannula 104 and the arm 1208 extends through the wall of the cannula 104 via a slider track 1210 defined in the cannula 104. The slider track 1210 extends longitudinally and thereby allows the retention sled 1200 to move axially in the proximal and distal directions as the arm 1208 translates within the slider track 1210.

The head 1206 may be received within a retention channel 1212 defined on the backside of the radial support member 1202. The retention channel 1212 also extends longitudinally, which allows the radial support member 1202 to move axially in the proximal and distal directions relative to the retention sled 1200 as the head 1206 translates within the retention channel 1212.

In some embodiments, as illustrated, the radial support member 1202 may provide and otherwise define an angled upper surface 1214 and the retention channel 1212 may transition into an angled portion 1216 contiguous with the angled upper surface 1214. As discussed below, the angled upper surface 1214 and the angled portion 1216 of the retention channel 1212 may prove advantageous in cooperatively allowing the radial support member 1202 to exit the bottom of the cannula 104 and move (transition) radially outward, which allows longitudinal passage of larger-diameter surgical tools through the cannula 104.

Figure 13A:
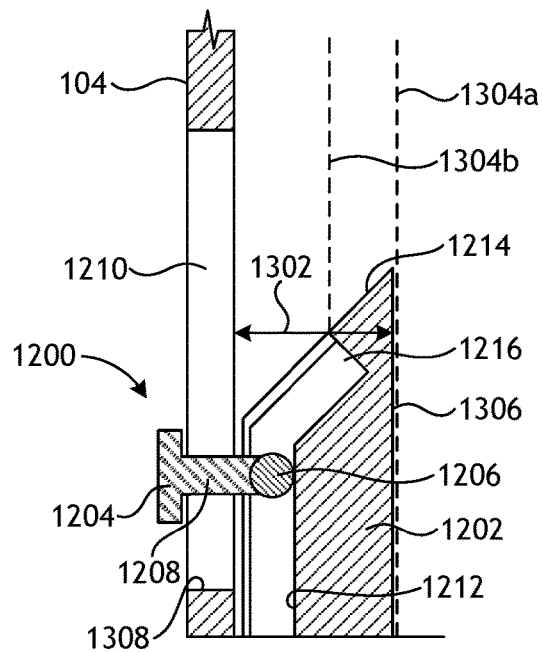
FIG. 13A is a cross-sectional side view of the retention sled of FIG. 12.

FIG. 13A is a cross-sectional side view of the retention sled 1200 as shown in FIG. 12. As illustrated, the slider 1204 is positioned on the exterior of the cannula 104, the arm 1208 extends through the slider track 1210, and the head 1206 is received within the retention channel 1212 defined on the backside of the radial support member 1202. The radial support member 1202 extends radially inward from the inner wall of the cannula 104 to a depth 1302. In operation, the radial support member 1202 may be configured to radially support a first surgical tool 1304a (shown in dashed lines) having a first diameter. In some embodiments, the first surgical tool 1304a may comprise the first surgical tool 1108a of FIG. 11B. When the first surgical tool 1304a is introduced into the cannula 104 and extended through the radial support assembly 1200, an inner surface 1306 of the radial support member 1202 engages or comes into close contact with the outer radial surface of the first surgical tool 1304a. The radial support member 1202 operates to generally center the first surgical tool 1304a within the cannula 104, and thereby eliminate or significantly minimize unintended oscillation and/or vibration of the first surgical tool 1304a.

In contrast, when a second surgical tool 1304b (shown in dashed lines) having a larger diameter that the first surgical tool 1304a is introduced into the cannula 104, the second surgical tool 1304b will axially engage the radial support member 1202 at the angled upper surface 1214. In some embodiments, the second surgical tool 1304b may comprise the second surgical tool 1108b of FIGS. 11B-11C. To advance the second surgical tool 1304b further distally, the radial support member 1202 will be forced out of the cannula 104.

Ejection of the radial support member 1202 can be accomplished by placing an axial load on the radial support member 1202 in the distal direction with the second surgical tool 1304b, which urges the radial support member 1202 and the retention sled 1200 in the same distal direction. The slider 1204 may be able to move longitudinally until the arm 1208 bottoms out at a bottom 1308 of the slider track 1210. Once the arm 1208 bottoms out, the head 1206 may move longitudinally within the retention channel 1212 until encountering the angled portion 1216. The retention channel 1212 and the angled upper surface 1214 may be configured (designed) such that when the slider 1204 bottoms out at the bottom 1308 and the head 1206 reaches the angled portion 1216, the angled upper surface 1214 may have started to exit the cannula 104. As a result, as the second surgical tool 1304b continues advancing in the distal direction, the head 1206 may be able to transition into the angled portion 1216 and the angled upper surface 1214 allows the radial support member 1202 to move radially outward outside of the cannula 104. Accordingly, the angled upper surface 1214 and the angled portion 1216, in conjunction with the retention sled 1200, cooperatively allow the radial support member 1202 to exit the bottom of the cannula 104 and move radially outward, which allows longitudinal passage of the second surgical tool 1304b through the cannula 104.

Advantageously, the foregoing steps may be reversed to place the radial support member 1202 back within the cannula 104. In at least one embodiment, a user (e.g., a surgeon) may manually move the radial support member 1202 back into the cannula 104 by pushing on the bottom of the radial support member 1202.

Figure 13B:
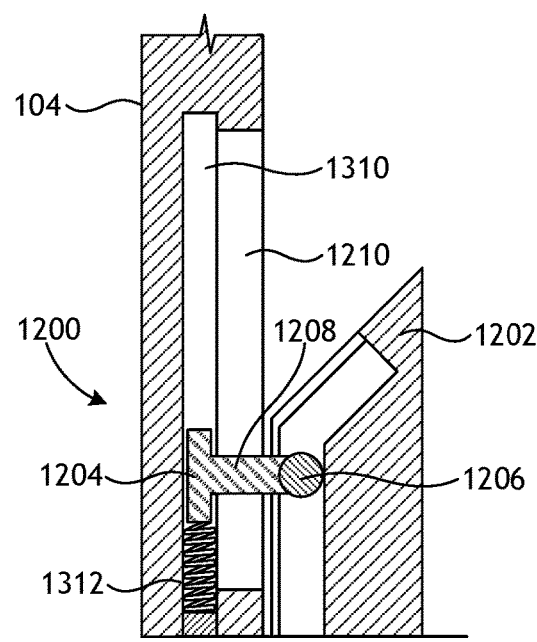
FIGS. 13B and 13C are cross-sectional side views of variations of the retention sled of FIG. 12.

FIG. 13B is a cross-sectional side view of an alternative embodiment of the retention sled 1200 of FIG. 12. The retention sled 1200 shown in FIG. 13B may be similar in most respects to the retention sled 1200 shown in FIG. 13A and therefore will be best understood with reference thereto, where like numerals represent like elements. Unlike the embodiment shown in FIG. 13A, the slider 1204 shown in FIG. 13B is positioned (arranged) within an internal channel 1310 defined in the wall of the cannula 104. The internal channel 1310 communicates with the slider track 1210 and allows the retention sled 1200 to move axially in the proximal and distal directions as the arm 1208 translates within the slider track 1210.

Operation of the retention sled 1200 shown in FIG. 13B is substantially similar to operation of the retention sled 1200 shown in FIG. 13A. Unlike the embodiment of FIG. 13A, however, the retention sled 1200 of FIG. 13B may further include a biasing device 1312 arranged within the internal channel 1310. In the illustrated embodiment, the biasing device 1312 is a compression spring, but could alternatively be any other mechanism or device that provides an axial biasing force against the slider 1204.

The biasing device 1312 may prove advantageous in helping cause reversibility of the retention sled 1200. More specifically, a surgical tool may be large enough to push the radial support member 1202 out of the cannula 104, as described above with reference to FIG. 13A, but the biasing device 1312 may be configured to provide an axial biasing force on the retention sled 1200 in the proximal direction, which may help return the radial support member 1202 back within the cannula 104. The axial biasing force acts on the slider 1204, which transfers the force to the radial support member 1202 via the head 1206 received within the angled portion 1216 and urges the radial support member 1202 back in the proximal direction. Accordingly, a surgical tool advanced distally within the cannula 104 may overcome the axial biasing force in the distal direction, but once the surgical tool is removed from the cannula 104, the axial biasing force may help transition the radial biasing element 1202 back into the cannula 104.

Figure 13C:
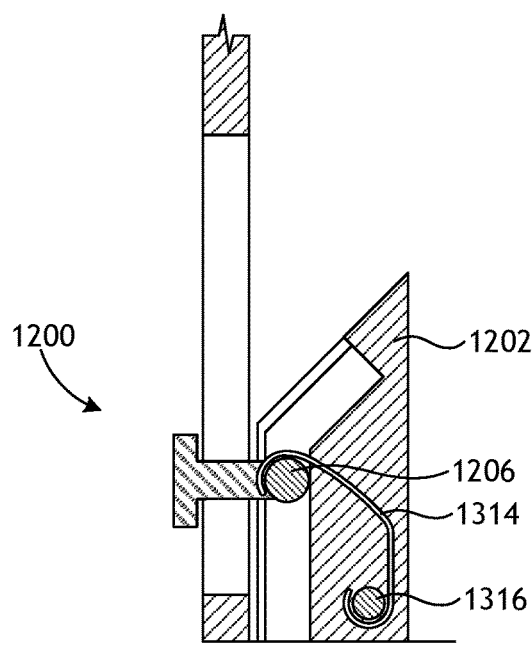

FIG. 13C is a cross-sectional side view of another alternative embodiment of the retention sled 1200 of FIG. 12. The retention sled 1200 shown in FIG. 13C may be similar in most respects to the retention sled 1200 shown in FIG. 13A and therefore will be best understood with reference thereto, where like numerals represent like elements. Unlike the embodiment shown in FIG. 13A, the retention sled 1200 of FIG. 13C includes a biasing device 1314 used to facilitate reversibility of the retention sled 1200.

The biasing device 1314 may comprise, for example, a constant force spring or the like. The biasing device is shown in FIG. 13C in a natural state and may be made of a resilient material that returns the biasing device 1314 to the natural state when unaffected by any external forces. In at least one embodiment, the biasing device 1314 may be made of spring steel.

The biasing device 1314 is coupled to and extends between the head 1206 and a pin 1316 coupled to the radial support member 1202. Operation of the retention sled 1200 of FIG. 13C is substantially similar to operation of the retention sled 1200 shown in FIG. 13A. However, unlike the embodiment of FIG. 13A, the biasing device 1314 may prove advantageous in helping cause reversibility of the retention sled 1200. More specifically, a surgical tool may be large enough to push the radial support member 1202 out of the cannula 104, as described above with reference to FIG. 13A, but the biasing device 1314 may be configured to return to the natural state once the surgical tool is removed from the cannula 104. As the biasing device 1314 returns to the natural state, the radial support member 1202 is simultaneously pulled back into the cannula 104 and to its original position.

Embodiments disclosed herein include:

A. A trocar assembly that includes a trocar housing that defines a working chamber, a cannula having a proximal end and a distal end, wherein the cannula is coupled to the trocar housing at the proximal end to facilitate communication between the cannula and the working chamber, and a radial support assembly arranged at or near the distal end and including a plurality of radial support members that extend radially inward toward a centerline of the cannula to center a surgical tool within the cannula and thereby minimize unintended oscillation and vibration of the surgical tool.

B. A method of using a trocar assembly that includes introducing a surgical tool into a working chamber defined by a trocar housing that communicates with a cannula coupled to the trocar housing, wherein a radial support assembly is arranged at or near a distal end of the cannula and includes a plurality of radial support members that extend radially inward toward a centerline of the cannula, extending the surgical tool into the cannula, and engaging an outer surface of the surgical tool with the plurality of radial support members and thereby centering the surgical tool within the cannula and minimizing unintended oscillation and vibration of the surgical tool.

Each of embodiments A and B may have one or more of the following additional elements in any combination: Element 1: wherein the cannula includes a first cannula portion and a second cannula portion separated by a gap, and the trocar assembly further comprises a plurality of support columns extending between and connecting the first and second cannula portions, wherein each radial support member is arranged within the gap and mounted to a corresponding one of the plurality of support columns. Element 2: further comprising a longitudinal slot defined in each radial support member, wherein each longitudinal slot is sized to receive the corresponding one of the plurality of support columns, and a biasing device that interposes each radial support member and the corresponding one of the plurality of support columns to compliantly urge each radial support member toward the centerline. Element 3: wherein each radial support member further define an inner surface engageable with an outer radial surface of the surgical tool, and wherein each inner surface transitions into a beveled surface that helps the radial support assembly receive the surgical tool. Element 4: further comprising a plurality of windows defined in the cannula at or near the distal end, wherein each window is shaped to receive and seat a corresponding one of the plurality of radial support member columns. Element 5: further comprising a tab defined by each window, a pocket defined on each radial support member and alignable with the tab, and a biasing device received within the pocket of each radial support member and interposing the tab and the corresponding one of the plurality of radial support members to compliantly urge each radial support member toward the centerline. Element 6: wherein each window defines two longitudinal slots separated by a central portion, the trocar assembly further comprising a pocket defined on each radial support member and alignable with the central portion, and a biasing device received within the pocket of each radial support member and interposing the tab and the corresponding one of the plurality of radial support members to compliantly urge each radial support member toward the centerline. Element 7: wherein the radial support assembly is arranged within the cannula at or near the distal end and the plurality of radial support members comprise keystones arranged side by side to form a ring within the cannula. Element 8: wherein the plurality of radial support members comprise a first plurality of radial support members extending from an inner radial surface of the cannula toward the centerline to a first radial depth, and a second plurality of radial support member extending from the inner radial surface toward the centerline to a second radial depth smaller than the first radial depth. Element 9: wherein the first and second pluralities of radial support members are releasably attached to the inner radial surface. Element 10: wherein the plurality of radial support members are made of a biodegradable material. Element 11: further comprising a retention sled coupled to a corresponding one of the plurality of radial support members to retain the corresponding one of the plurality of radial support members when forced out of the cannula by the surgical tool. Element 12: wherein the retention sled comprises a slider, an arm that extends from the slider and through a slider track defined in a wall of the cannula, and a head arranged at an end of the arm and received within a retention channel defined on a backside of the corresponding one of the plurality of radial support members. Element 13: wherein the corresponding one of the plurality of radial support members defines an angled upper surface and the retention channel transitions into an angled portion contiguous with the angled upper surface, and wherein the angled upper surface and the angled portion of the retention channel cooperatively allow the corresponding one of the plurality of radial support members to exit the cannula and move radially outward. Element 14: further comprising a biasing device that urges the slider proximally relative to the cannula and thereby simultaneously urges the corresponding one of the plurality of radial support members back into the cannula when forced out of the cannula with the surgical tool.

Element 15: wherein the cannula includes a first cannula portion and a second cannula portion separated by a gap and a plurality of support columns extend between and connect the first and second cannula portions, and wherein each radial support member is arranged within the gap and mounted to a corresponding one of the plurality of support columns, the method further comprising receiving the corresponding one of the plurality of support columns in a longitudinal slot defined in each radial support member, and compliantly urging each radial support member toward the centerline with a biasing device that interposes each radial support member and the corresponding one of the plurality of support columns. Element 16: wherein a plurality of windows are defined in the cannula at or near the distal end and each window is shaped to receive and seat a corresponding one of the plurality of radial support member columns, the method further comprising aligning a pocket defined on each radial support member with a tab defined by each window, and compliantly urging each radial support member toward the centerline with a biasing device received within the pocket of each radial support member and interposing the tab and the corresponding one of the plurality of radial support members. Element 17: wherein the surgical tool is a first surgical tool having a first diameter and the plurality of radial support members comprise keystones that form a ring within the cannula, and wherein the plurality of radial support members comprise a first plurality of radial support members extending from an inner radial surface of the cannula toward the centerline to a first radial depth, and a second plurality of radial support member extending from the inner radial surface toward the centerline to a second radial depth smaller than the first radial depth, the method further comprising radially supporting the first surgical tool within the cannula with the first plurality of radial support members, introducing a second surgical tool having a second diameter greater than the first diameter into the cannula, axially engaging and forcing the first plurality of radial support members out of the cannula with the second surgical tool, and radially supporting the second surgical tool within the cannula with the second plurality of radial support members. Element 18: further comprising a retention sled coupled to a corresponding one of the first plurality of radial support members, the method further comprising retaining the corresponding one of the first plurality of radial support members forced out of the cannula with the second surgical tool, removing the second surgical tool from the cannula, and returning the corresponding one of the first plurality of radial support members back into the cannula.

By way of non-limiting example, exemplary combinations applicable to A and B include: Element 1 with Element 2; Element 1 with Element 3; Element 4 with Element 5; Element 4 with Element 6; Element 7 with Element 8; Element 8 with Element 9; Element 7 with Element 10; Element 7 with Element 11; Element 11 with Element 12; Element 12 with Element 13; Element 12 with Element 14; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any Element that is not specifically disclosed herein and/or any optional Element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the Elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an Element closer to the surgeon or the robotic manipulator and the term "distal" refers to the position of an Element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A trocar assembly, comprising:
   a trocar housing that defines a working chamber;
   a cannula having a proximal end and a distal end, wherein the cannula is coupled to the trocar housing at the proximal end to facilitate communication between the cannula and the working chamber; and
   a radial support assembly arranged at or near the distal end and including a plurality of radial support members that extend radially inward toward a centerline of the cannula to center a surgical tool within the cannula and thereby minimize unintended oscillation and vibration of the surgical tool,
   wherein an inner surface of each radial support member is arcuate to cradle an outside surface of the surgical tool, and wherein each inner surface transitions into a beveled surface that helps the radial support assembly receive the surgical tool.

2. The trocar assembly of claim 1, wherein the cannula includes a first cannula portion and a second cannula portion separated by a gap, and the trocar assembly further comprises:
   a plurality of support columns extending between and connecting the first and second cannula portions, wherein each radial support member is arranged within the gap and mounted to a corresponding one of the plurality of support columns.

3. The trocar assembly of claim 2, further comprising:
   a longitudinal slot defined in each radial support member, wherein each longitudinal slot is sized to receive the corresponding one of the plurality of support columns; and
   a biasing device that interposes each radial support member and the corresponding one of the plurality of support columns to compliantly urge each radial support member toward the centerline.

4. The trocar assembly of claim 1, further comprising a plurality of windows defined in the cannula at or near the distal end, wherein each window is shaped to receive and seat a corresponding one of the plurality of radial support member columns.

5. The trocar assembly of claim 4, further comprising:
   a tab defined by each window;
   a pocket defined on each radial support member and alignable with the tab; and a biasing device received within the pocket of each radial support member and interposing the tab and the corresponding one of the plurality of radial support members to compliantly urge each radial support member toward the centerline.

6. The trocar assembly of claim 4, wherein each window defines two longitudinal slots separated by a central portion, the trocar assembly further comprising:
   a pocket defined on each radial support member and alignable with the central portion; and
   a biasing device received within the pocket of each radial support member and interposing the tab and the corresponding one of the plurality of radial support members to compliantly urge each radial support member toward the centerline.

7. A method of using a trocar assembly, comprising:
   introducing a surgical tool into a working chamber defined by a trocar housing that communicates with a cannula coupled to the trocar housing, wherein a radial support assembly is arranged at or near a distal end of the cannula and includes a plurality of radial support members that extend radially inward toward a centerline of the cannula;
   extending the surgical tool into the cannula; and
   engaging an outer surface of the surgical tool with arcuate inner surfaces of the plurality of radial support members and thereby centering the surgical tool within the cannula and minimizing unintended oscillation and vibration of the surgical tool,
   wherein each inner surface transitions into a beveled surface that helps the radial support assembly receive the surgical tool.

8. The method of claim 7, wherein the cannula includes a first cannula portion and a second cannula portion separated by a gap and a plurality of support columns extend between and connect the first and second cannula portions, and wherein each radial support member is arranged within the gap and mounted to a corresponding one of the plurality of support columns, the method further comprising:
   receiving the corresponding one of the plurality of support columns in a longitudinal slot defined in each radial support member; and
   compliantly urging each radial support member toward the centerline with a biasing device that interposes each radial support member and the corresponding one of the plurality of support columns.

9. The method of claim 7, wherein a plurality of windows are defined in the cannula at or near the distal end and each window is shaped to receive and seat a corresponding one of the plurality of radial support member columns, the method further comprising:
   aligning a pocket defined on each radial support member with a tab defined by each window; and
   compliantly urging each radial support member toward the centerline with a biasing device received within the pocket of each radial support member and interposing the tab and the corresponding one of the plurality of radial support members.

* * * * *